United States Patent

Bhatt et al.

[11] Patent Number: 6,106,808
[45] Date of Patent: *Aug. 22, 2000

[54] HAIR SPRAY CONTAINING CARBOXYLATED POLYURETHANE RESINS

[75] Inventors: Darshna Bhatt, Schaumburg; Ramiro Galleguillos, Glendale Heights, both of Ill.

[73] Assignee: Helene Curtis, Inc., Chicago, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/717,105

[22] Filed: Sep. 20, 1996

[51] Int. Cl.⁷ ....................................... A61K 9/12
[52] U.S. Cl. .......................... 424/45; 424/47; 424/70.11
[58] Field of Search ................. 424/45, 47, DIG. 1, 424/DIG. 2, 70.11, 78.17, 78.37; 132/203

[56] References Cited

U.S. PATENT DOCUMENTS

| | | |
|---|---|---|
| 3,975,350 | 8/1976 | Hudgin et al. . |
| 4,156,066 | 5/1979 | Gould . |
| 4,359,558 | 11/1982 | Gould et al. . |
| 4,408,023 | 10/1983 | Gould et al. . |
| 4,424,305 | 1/1984 | Gould et al. . |
| 4,439,583 | 3/1984 | Gould et al. . |
| 4,439,585 | 3/1984 | Gould et al. . |
| 4,445,521 | 5/1984 | Grollier et al. . |
| 4,496,535 | 1/1985 | Gould et al. . |
| 4,729,914 | 3/1988 | Kliment et al. . |
| 4,743,673 | 5/1988 | Johnston et al. . |
| 4,780,512 | 10/1988 | Gould et al. . |
| 5,120,816 | 6/1992 | Gould et al. . |
| 5,164,177 | 11/1992 | Bhatt et al. . |
| 5,334,691 | 8/1994 | Gould et al. . |
| 5,639,448 | 6/1997 | Galleguillos et al. . |

FOREIGN PATENT DOCUMENTS

| | | |
|---|---|---|
| 0 619 111 | 10/1994 | European Pat. Off. . |
| 94/03510 | 2/1994 | WIPO . |

*Primary Examiner*—Thurman K. Page
*Assistant Examiner*—R. Bawa
*Attorney, Agent, or Firm*—Matthew Boxer

[57] ABSTRACT

A hair spray composition comprising:
(a) about 0.25% to about 6% by weight of a carboxylated polyurethane resin;
(b) 0% to about 6% by weight of a second hair fixative resin;
(c) 0% to about 80% by weight of an alcohol; and
(d) about 15% to about 99% by weight water,
  wherein the carboxylated polyurethane resin has a weight average molecular weight of about 10,000 to about 25,000, and is a reaction product of a mixture comprising:
  (i) about 10% to about 90% by weight of the mixture of a polyoxyalkylene diol having a number average molecular weight of about 400 to about 20,000;
  (ii) about 0.01% to about 20% by weight of the mixture of an alkylene glycol;
  (iii) about 3% to about 80% by weight of the mixture of an organic diisocyanate;
  (iv) about 0.1% to about 12% by weight of the mixture of a 2,2-di(hydroxymethyl)-alkanoic acid; and
  (v) about 0.1% to about 0.5% by weight of the mixture of water,
    wherein a ratio of isocyanate groups to hydroxyl groups is about 0.55 to about 0.75 is disclosed.

1 Claim, No Drawings

HAIR SPRAY CONTAINING CARBOXYLATED POLYURETHANE RESINS

FIELD OF THE INVENTION

The present invention is directed to hair spray compositions that are applied to the hair to maintain the hair in a predetermined shape or configuration. The compositions impart excellent hair set retention, feel, and washability to sprayed hair. In particular, the present invention relates to aerosol and nonaerosol hair spray compositions comprising a carboxylated polyurethane resin, an optional second hair fixative resin, an organic solvent, and water, wherein the composition preferably is free of a neutralizing agent for the polyurethane resin.

BACKGROUND OF THE INVENTION

Normal hair can be so fine, limp, and lacking in body that the hair does not hold a hair set well. Furthermore, hair can lose body and be weakened as a result of being subjected to chemically active hair treatments, such as permanent waves and tints. Additionally, hair can be weakened even further by other contributing factors, such as bleaching by the sun or chlorinated swimming pool water.

Hair setting is basically the process of shaping wet hair by the steps of stretching the hair by curling the hair, fixing the hair in place by drying, then combing to give the finishing touches to provide the desired hairstyle. In particular, the setting of wet hair can be accomplished by making flat curls from strands of hair and fixing the curls with hairpins to product "pin curls." Similarly, wet hair can be set by using any of a variety of rollers or curlers to mechanically fix the hair. In either case, winding of wet hair is followed by drying, either ambient air drying, electric drying, or hot air, i.e., blow, drying.

The inherent problem encountered in hair setting is the natural tendency of hair to return to its natural shape. For example, set hair returns to its natural shape almost immediately if moistened. Likewise, high humidity conditions accelerate the tendency of hair to return to its natural shape. Therefore, intensive efforts have been directed toward providing a hair set with sufficient holding power to maintain a desired hairstyle until at least the next shampoo, and, therefore, giving the hair set a degree of permanency.

As indicated by the tendency of hair to return to its natural shape, hair is an elastic structure. As a result, slight deformations in hair structure resulting from setting the hair are completely reversible. However, the rate of return of hair to its natural shape is dependent upon the method used to deform, or set, the hair. Hair sets performed on wet strands of hair being rolled tightly, either in curls around the finger or on curlers, followed by drying the hair and unrolling the curlers after drying, corresponds to the release of the hair from a deformation-causing load. The deformation, or set, obtained can last for several days, but the set will not be retained if the hair is wetted.

Investigators have sought to delay the combined action of natural forces and moisture that cause hair to return to its original state by applying solutions containing naturally occurring or synthetic polymers after the hair is shaped into a desired configuration. When applied to shaped hair from aqueous or aqueous/alcoholic solutions, the polymers form a film on the hair, after drying, to help maintain the hair in the previously shaped configuration. The polymeric film promotes cohesion and gives stability to the hair set to maintain hold of the set. The principal objective of a setting lotion is to cover the previously styled hair with an invisible polymeric film that gives the styled hair a degree of rigidity and protects the hairstyle against wind and humidity.

Hair spray products act in a similar manner. Hair spray products are applied to wet and/or dry hair and contain a polymer, or mixtures of polymers, that remain fixed on the previously styled hair and effect the hair in various ways. For example, a "mechanical" effect is exerted on each individual hair. The film-forming polymers are used to provide a flexible sheath of polymeric film on the shaped hair after drying, and, therefore, for mechanical reasons, retard the return of each individual hair to its natural shape. In addition, the polymeric film provides an overall stiffening of the hair. The hair behaves as if the individual hair strands are welded together, and the final hairstyle has better cohesion, therefore, resisting the natural forces that return the hair to its natural shape. Finally, the polymeric film protects the hair from humidity. The ability of the polymeric film to attract and absorb water preferably is minimal, such that the polymeric film retards moisture uptake by the hair and retards return of the hair to its natural state.

The general principles of hair setting are thoroughly discussed by C. Zviak, in *The Science of Hair Care*, Marcel Dekker, pp. 149–181 (1986). Zviak reviews both the polymers used in hair setting products and the formulation principles used to produce a hair set product that provides such beneficial hair set properties as improved hairstyle hold, easy application and combing, quick drying and nonstickiness, good hair body and bounce, increased hair volume and gloss, and hydrophobicity. It is evident, however, that when formulating a hair styling product, some of these benefits must be sacrificed to some degree to achieve a competing benefit. Therefore, the formulation of hair styling products has proved difficult.

In particular, a consumer-acceptable hair spray should effectively retain the hairstyle, and should impart a natural feel to the hair. Conventional hair fixative resins provide good hair set retention at the expense of hair feel, i.e., the hair feels rough, stiff, and crunchy. Investigators attempted to improve the feel of hair sprayed with conventional resins by incorporating a low molecular weight plasticizing compound into the hair spray. However, the hair fixative resins were softened and did not impart sufficient style retention to the sprayed hair.

Investigators also tested resins having a glass transition temperature (Tg) below 0° C. Such resins are pliable, and, therefore, feel soft on the hair. However, the low Tg resins did not provide sufficient hair set retention.

To overcome some of the inherent disadvantages of the polymers utilized to set the hair, hair set products are made available in diversified forms in an attempt to minimize the drawbacks of the particular polymer used in the formulation. For example, hair set products are available as plasticizing lotions, plasticizing gels, aerosol foams, all-purpose lotions, hair sprays, holding lotions, conditioners, and shampoos.

Nonionic, cationic, and anionic polymers have been used in hair set products, with the anionic polymers providing the best hair set results. However, anionic polymers also have disadvantages, such as high water solubility, and, therefore, low hydrophobicity, and low substantivity on hair fibers, and, therefore, causing a crust and flaking due to easy elimination from the hair by combing and brushing. As a result, investigators have continued to search for compounds and compositions that provide the primary benefit of improved durability of the hair set.

Therefore, the use of resins, or polymers, in hair sprays is well known, as summarized in Grollier et al. U.S. Pat. No. 4,445,521. The resins typically used in hair sprays are linear vinyl (e.g., an alkyl vinyl ether) or acrylic (e.g., an alkyl acrylate)polymers prepared by copolymerizing two or more monomers in a free radical polymerization reaction. The vinyl and acrylic-based resins are used in relatively high concentrations in a hair spray composition to fix the hair in a particular configuration and to provide good hair set retention. However, at high concentrations, the vinyl and acrylic-based resins exhibit disadvantages that adversely affect the hair, such as poor combing and feel, and excessive stiffness, crust, and flaking.

The vinyl and acrylic-based hair fixative resins typically used in hair sprays were designed for use in anhydrous alcoholic hair spray compositions. The resins, therefore, have excellent compatibility with, and solubility in, alcohols (e.g., ethanol) used in pump spray compositions and hydrocarbons used as propellants in aerosol compositions. However, due to environmental and toxicological concerns, government regulations require a decrease in the amount of organic solvents used in hair spray and related compositions. Therefore, the alcohols and the hydrocarbon gases traditionally present in hair spray compositions are being replaced with water and water-soluble solvents, like dimethyl ether, that pose less harm to the environment.

The solvent changes required by government regulation made the traditional vinyl and acrylic-based resins unsuitable in hair spray compositions. For example, the presence of water in a hair spray composition increases the viscosity of the composition, thereby making spraying difficult to impossible when traditional resins are used. The relatively high viscosity of such compositions requires a reduction in the resin concentration of the composition, which, in turn, results in insufficient hair set retention. The presence of water also increases the tackiness of the resin on the hair, thereby prolonging the drying time of the hair spray on the hair. Water further reduces the hair-wetting ability of the compositions, resulting in beading and flaking of the resin from the hair. In the case of aerosol products, the combination of water, resin, and propellant gas results in poor delivery and foaming of the composition, large aerosol particle size, and beading of the resin.

The need to change solvent systems for hair sprays again led investigators to search for new hair setting resins that overcome the disadvantages associated with the vinyl and acrylic resins. As set forth in European Patent Application 0 619 111, one class of resins is the polyurethanes. However, the hair fixative compositions disclosed in EP 0 619 111 require a base to neutralize, and solubilize, the polyurethane resin. It would be desirable to provide an aqueous hair spray composition containing a low amount of volatile organic compounds (VOC), that is free of a base, and that overcomes that disadvantages associated with traditional vinyl and acrylic resins.

SUMMARY OF THE INVENTION

The present invention is directed to aerosol and nonaerosol (i.e., pumpable) hair spray compositions containing hydrophilic, carboxylated polyurethane resins. The hair spray compositions impart good hair set retention and natural feel to sprayed hair, and provide superior retention of the hairstyle at high relative humidity. Such results are unexpected because traditional hair setting resins are hydrophobic. In contrast, the carboxylated polyurethane resins are hydrophilic, yet provide good hair set retention, while imparting a soft, natural, and nontacky feel to treated hair. The carboxylated polyurethane resins are soluble in water and in a wide range of water-to-alcohol ratios, without the need to neutralize the resin with a base. Therefore, the hair spray compositions contain a low amount of VOC and are safe to the environment.

The carboxylated polyurethane resins have a low Tg and are pliable at room temperature, and, therefore, feel soft and natural to the touch, but are not tacky. The polyurethane resins deliver a good hair set retention, and because aqueous and hydroalcoholic solutions of the polyurethane resins have a low viscosity, hair spray compositions containing the polyurethane resin have an excellent spray pattern from aerosol and nonaerosol containers. The polyurethane resins exhibit minimal crust and flaking, and are washable from the hair. Finally, to satisfy differing consumer preferences, the properties of the polyurethane resins can be modified by incorporating an optional second hair fixative resin into the hair spray composition. For example, the stiffness of sprayed hair can be increased, thereby giving the consumer a "signal" that the hair has been treated with a hair spray.

In particular, the present invention is directed to hair spray compositions comprising: (a) about 0.25% to about 6%, by total weight of the composition, of a carboxylated polyurethane resin, (b) 0% to about 6%, by total weight of the composition, of an optional second hair fixative resin, (c) 0% to about 80%, by total weight of the composition, of an alcohol, like ethanol, and (d) about 15% to about 99%, by total weight of the composition, of water. The hair spray compositions have a pH of about 6 to about 10. The hair spray compositions do not require a base to solubilize the carboxylated polyurethane resin in water.

The composition can be applied to the hair as a pump spray. Alternatively, if an aerosol composition is desired, the composition can further comprise about 5% to about 30%, by total weight of the composition, of a propellant. Optional ingredients also can be incorporated into the hair spray composition.

The polyurethane resin, also termed a polycarbamyl polyglycol, incorporates carboxyl groups and is hydrophilic. The polyurethane resins have excellent tear strength, excellent washability, good adhesion, and are soluble in water and polar solvents, thereby making them useful in hair spray compositions. The ability of a carboxylated polyurethane resin to impart good hair set retention properties to hair is unexpected. Traditional hair fixative resins are hydrophobic in order to prevent the absorption of water and destruction of the hair set. In contrast, the polyurethane resins are hydrophilic, and have the ability to absorb water and give the hair a soft, nontacky, natural feel, while also imparting good hair set retention properties to sprayed hair. In addition, the polyurethane resins form clear, low viscosity, solutions in neutral to slightly basic aqueous solvents. Solutions of the hydrophilic polyurethane resins, therefore, are sprayable and form elastic films that give treated hair a natural feel. The optional second hair fixative resin gives treated hair a desired degree of stiffness.

In accordance with an important aspect of the present invention, hair spray compositions exhibit excellent sprayability when the viscosity of a 55% by weight VOC composition is about 1 to about 10 cps or about 1 to about 25 cps for an 80% by weight VOC composition. Compositions having such a viscosity provide a spray particle size of about 20 to about 150 microns.

In accordance with another important aspect of the present invention, the hair spray compositions exhibit improved washability from the hair when the carboxylated polyurethane resin has an acid value of at least about 7 mg KOH/g (milligrams potassium hydroxide per gram of resin), and preferably about 7 to about 50 mg KOH/g of resin.

In accordance with one embodiment of the present invention, the carboxylated polyurethane resins used in the hair spray composition have a weight average molecular weight ($M_w$) of about 10,000 to about 25,000, and are produced by reacting: (a) a diol component comprising one or more polyoxyalkylene diols; (b) an alkylene glycol; (c) a diisocyanate; (d) water in an amount of about 0.1% to about 0.5% of the combined weight of the reactants; and (e) a 2,2-di(hydroxymethyl)alkanoic acid, preferably 2,2-di-(hydroxymethyl)propionic acid, wherein the ratio of NCO (isocyanate) groups to OH (hydroxyl) groups in the water, diol, and glycol mixture, i.e., the R-value, is about 0.55 to about 0.75.

The hydrophilic carboxylated polyurethane resin contains polyoxyalkylene units, i.e., soft segments, and alkylene units, i.e., hard segments, connected through urethane linkages. Also incorporated into the polymer chain is a small amount of diol having a pendant carboxyl group. The polymer chain also contains urea linkages resulting from a reaction between the water and isocyanate groups, which modify the hair styling properties of the carboxylated polyurethane resin.

The polyoxyethylene soft segments of the polyurethane resin impart hydrophilicity to the polyurethane. Soft segments derived from polyoxypropylene and polyoxytetramethylene diols provide a softer, but less hydrophilic, polyurethane. Hydrophilic pqlyurethane resins having improved strength and superior adhesive properties can be formed by using mixtures of polyoxyalkylene diols.

In another embodiment of the present invention, the carboxylated polyurethane resins used in the hair spray composition are produced from (a) a major portion of polyoxyethylene diol having a number molecular weight ($M_n$) of 6000 to 10,000; (b) an alkylene glycol, preferably diethylene glycol, cyclohexanedimethanol, or dipropylene glycol; (c) a diisocynanate; (d) water in the amount of about 0.1% to about 0.5% by weight; and (e) a 2,2-di-(hydroxymethyl)alkanoic acid, wherein the ratio of NCO to OH in the water, diol, and glycol mixture (i.e., the R-value) is about 0.55 to about 0.75. These polyurethane resins are soluble in dilute (neutral to basic) aqueous solutions, and exhibit good spray-ability, superior feel, low flaking, desirable crust, and good set retention when applied to hair. The polyurethane resins are hydrophilic, and provide a soft feel in a hydrated state. In a particular embodiment of a polyurethane resin produced with a major portion of polyoxyethylene diol, water is added in the amount of about 0.15% to about 0.45% by weight, and the ratio of NCO to OH of the water, diol and glycol mixture (i.e., the R-value) is about 0.55 to about 0.75 to provide a carboxylated polyurethane resin having improved adhesiveness to the hair and improved slip, i.e., good combing properties.

Another aspect of the present invention is to provide a hair spray composition that provides good hair set retention at high relative humidity and that imparts a natural feel to the hair. Accordingly, a hydrophilic polyurethane resin incorporated into a present hair spray composition is pliable at room temperature and has an $M_w$ of about 10,000 to about 25,000, and preferably about 13,000 to about 24,000. Preferred carboxylated polyurethane resins have an R-value of about 0.57 to about 0.74.

In accordance with another important aspect of the present invention, hair spray compositions of the present invention incorporating a carboxylated polyurethane resin having an $M_w$ of about 10,000 to about 25,000 and an R-value of about 0.63 to about 0.75 provide sprayed hair having excellent feel and set retention, and a low amount of flaking and crust. Such hair spray compositions, therefore, meet all the criteria for a consumer-acceptable hair spray composition.

Furthermore, the feel of the sprayed hair can be modified to satisfy the differing tastes of consumers, especially with respect to stiffness of the sprayed hair, by incorporating an optional second hair fixative resin into the composition. The second hair fixative resin is a traditional vinyl or acrylic resin. The presence of a second hair fixative resin increases the stiffness of the hair, but does not adversely affect the advantageous properties imparted to the hair by the carboxylated polyurethane resin.

DETAILED DESCRIPTION OF THE INVENTION

The present hair spray compositions are sprayable hair styling aids containing a carboxylated polyurethane resin, and, if desired, an optional second hair fixative resin. The carboxylated polyurethane resins are soluble in water and in a broad range of water/alcohol mixtures, thereby permitting the preparation of aerosol and nonaerosol, i.e., pump spray, compositions containing a reduced amount of volatile organic compounds (VOC). The hair spray compositions also can contain propellant gases, and can be applied as an aerosol spray. The carboxylated polyurethane resins possess thermal properties that allow styling of the hair with curling irons and blow dryers. The polyurethane resin-based hairstyle compositions, therefore, overcome problems and disadvantages associated with prior acrylic and vinyl-based hair fixative resins, and provide improved styling, hair set retention, hair feel, washability, and spray properties.

In particular, the present hair spray compositions comprise about 0.25% to about 6%, and preferably about 0.5% to about 6%, by total weight, of a carboxylated polyurethane resin. To achieve the full advantage of the present invention, the composition comprises about 1% to about 5%, by weight of the composition, of a carboxylated polyurethane resin.

The polyurethane resins are linear, hydroxyl-terminated copolymers having pendant carboxyl groups. In accordance with an important feature of the present invention, the polyurethane resins can be solubilized in water, or in a hydroalcoholic solution, in the absence of a base.

The carboxylated polyurethane resins are soft and flexible, and have a melting point of about 40° C. to about 100° C., and preferably about 40° C. to about 90° C. To achieve the full advantage of the present invention, the polyurethane resins have a melting point of about 40° C. to about 80° C.

The carboxylated polyurethane resins also are (a) sprayable, (b) soluble in hydroalcoholic solutions, (c) propellant tolerant, and (d) fast drying. The polyurethane resins also exhibit good wet combing properties, and are washable from the hair.

A polyurethane resin incorporated into a present hair spray composition comprises a reaction product of a diol component, an alkylene glycol, an aliphatic diisocyanate, water, and a 2,2-di-(hydroxy-methyl)alkanoic acid. Alternatively, an amine, such as diglycolamine, can be substituted for at least a portion of the water in the reaction mixture. Aqueous solutions of the hydrophilic carboxylated polyurethane resins are pliable at room temperature, have low viscosities, and impart a soft feel, good set retention, reduced flaking and crust, and improved hair conditioning properties to sprayed hair.

In one embodiment, the polyurethane resin comprises the reaction product of: a diol component comprising a polyoxyalkylene diol, preferably a polyoxyethylene diol having an $M_n$ of about 400 to about 20,000, a polyoxypropylene diol having an $M_n$ of about 200 to about 2500, a block copolymer of ethylene oxide and propylene oxide having an $M_n$ of about 1,000 to about 9,000, or a polyoxytetramethylene diol having an $M_n$ of about 200 to about 4,000; about 0.01% to about 10% by weight of a low molecular weight alkylene glycol, for example, ethylene glycol, propylene glycol, 2-ethyl-1,3-hexanediol, tripropylene glycol, triethylene glycol, 2,4-pentanediol, 2-methyl-1,3-propanediol, 2-methyl-1,3-pentanediol, cyclohexanediol, cyclohexanedimethanol, dipropylene glycol, diethylene glycol, and mixtures thereof; an organic diisocyanate; a 2,2-di-(hydroxymethyl)alkanoic acid; and water in an amount of about 0.1% to about 0.5% by weight of the reaction mixture, wherein the NCO/OH ratio (i.e., the R-value) is about 0.55 to about 0.75, and preferably about 0.57 to about 0.74.

An amine can be used in the reaction mixture for at least a portion of the water. The amine can be added to the reaction mixture in an amount of about 0.01% to about 0.8% by weight amine, preferably about 0.02% to about 0.5% amine to about 0.01% to about 0.2% water in the reaction mixture. Amines that can be used in the reaction are ethylenediamine, propylenediamine, monoethanolamine, diglycolamine, and JEFFAMINE D1-230, D-400, D-2000, D-4000, ED-0600, ED-900, or ED-2001. The hydroxylamines and the JEFFAMINE products are manufactured by Texaco Chemical Company. Preferably, the amine is a hydroxylamine, and most preferably the amine is monoethanolamine and/or diglycolamine.

The polyoxyethylene diols are available from Union Carbide Corporation under the trademark CARBOWAX, such as CARBOWAX® 8000 and CARBOWAX® 1450 wherein the number represents number average molecular weight. The polyoxypropylene diols (PPG) are available from various sources, such as the PPG series of ARCO NIAX® PPG 1025, PPG 425, PPG 725, PPG 1225 and PPG 2025 and as R2134 (2200) and R2135 (4400), wherein the number represents number average molecular weight. Triols also are available from ARCO as NIAX® Polyols 11-34, LG-650, LG-56, LG-168, LHT-28, LHT-240. The polyoxytetramethylene diols are available from E.I. DuPont de Nemours as TERATHANE 600, 1000, 1400, 2000, and 2900. Polyetherpolycarbonate is available from BASF under the tradenames polytetrahydrofuran 1000 CD and 2000 CD.

A block polyoxyalkylene polymer also can be used in the reaction. For example, a propylene oxide terminated block of ethylene glycol manufactured by BASF under the tradename PLURONIC R and an ethylene oxide terminated block of propylene glycol manufactured by BASF under the tradename of PLURONIC can be used for the polyoxyalkylene in the reaction. Examples of the block copolymers of the sequential addition of ethylene oxide and propylene oxide to ethylene diamine are made by BASF under the tradename of PLURONIC, such as PLURONIC F68, F64, F127, L35, L92, L82, 17R2, and 25R2.

Preferably, the polyoxyalkylene diol used in forming the hydrophilic polyurethane resin is a polyoxyethylene diol. The blends of polyoxyalkylene diols contain at least about 10% polyoxyethylene diol, preferably, at least about 20% polyoxyethylene diol, and most preferably, at least about 25% polyoxyethylene diol, by weight.

The amount of polyoxyalkylene diol having a molecular weight of 400 to 20,000 in the polyurethane resin can vary from about 10% to about 90%, preferably about 30% to about 90%, and most preferably about 40% to about 90% by weight, and the number average molecular weight ($M_n$) of the polyoxyalkylene diol can vary from about 400 to about 20,000, preferably from about 400 to about 12,000, and more preferably from about 800 to about 10,000.

The alkylene glycols can be purchased from numerous sources. For example, propylene glycol can be purchased from Aldrich Chemical Company as 1,2-propanediol. The amount of the alkylene glycol (hard segment) component in the polyurethane resin can be about 0.01% to about 20%, preferably about 0.05% to about 15%, more preferably about 0.1% to about 12%, still more preferably about 0.5% to about 10%, and most preferably about 1% to about 8%, by weight of the reaction mixture.

The diisocyanate in the reaction mixture can be an aliphatic diisocyanate, an aromatic diisocyanate, or a mixture thereof. The aliphatic diisocyanates are preferred. An especially preferred diisocyanate is methylene bis(cyclohexyl-4-isocyanate). Other examples of diisocyanates are trimethylhexamethylene diisocyanate and isophorone diisocyanate. Representative examples of the preferred aliphatic diisocyanates include, but are not limited to tetramethylene diisocyanate, hexamethylene diisocyanate, trimethylene diisocyanate, cyclohexane-1,2-diisocyanate, and cyclohexane-1,4-diisocyanate. Examples of aromatic diisocyanates include 2,4-toluene diisocyanate and 2,6-toluene diisocyanate. Also suitable are the isocyanate equivalents which form urethane linkages, exemplified by nitrile carbonates, such as adiponitrile carbonate of U.S. Pat. No. 4,810,543, incorporated herein by reference. The amount of diisocyanate varies from about 3% to about 80%, preferably from about 4% to about 70%, more preferably from about 5% to about 60%, still more preferably from about 6% to about 55%, and most preferably from about 6.5% to about 50%, by weight. The polyurethane resins are prepared by reacting the polyoxyalkylene diols with the diisocyanates.

The amount of water in the reaction mixture is about 0.01% to about 0.75%, and more preferably about 0.35% to about 0.55%, by weight, of the reaction mixture.

The amount of 2,2-di-(hydroxymethyl)alkanoic acid in the reaction mixture is about 1% to about 12%, preferably about 1.5% to about 8%, and most preferably about 2% to about 6%, by weight. Preferably the 2,2-di-(hydroxymethyl) alkanoic acid is dimethylolpropionic acid. The final reaction product has an acid value of at least about 0.2, preferably at least about 0.5, and more preferably at least about 1.

The ratio of NCO to OH groups from the diol, alkylene glycol, amines and water (i.e., the R-value) in the reaction mixture is about 0.55 to about 0.75, and preferably from about 0.57 to about 0.74. The weight average molecular weight ($M_w$) of the carboxylated polyurethane resin is about 10,000 to about 25,000, and preferably about 13,000 to about 24,000. Alternatively stated, the z-average molecular weight ($M_z$) of the carboxylated polyurethane resin is about 15,000 to about 45,000, and preferably about 20,000 to about 40,000. The sum of all ingredients, including the diols, glycols, water, and diisocyanate in the reaction mixture totals 100% by weight.

In another embodiment, the hydrophilic polyurethane resin comprises a reaction product of: (a) a diol having a major portion of a polyoxyethylene diol having an $M_n$ of 6,000 to 10,000, and a minor portion of a polyoxypropylene diol having an $M_n$ of about 1,000 to about 3,500, a polyoxyethylene diol having an $M_n$ of about 600 to about 2000, or a mixture thereof; (b) an alkylene glycol; (c) a diisocyanate; (d) water in an amount of about 0.1% to about 0.5% by weight of the reaction mixture; and (e) a 2,2-di-(hydroxymethyl)alkanoic acid, and an equivalent mole weight ratio of NCO to OH of the water, diol and glycol of about 0.55 to about 0.75. Preferably at least 45% by weight of the polyoxyethylene glycol of $M_n$ about 8000, more preferably at least about 55%, still more preferably at least about 65%, and most preferably at least 75%, is used in the total reaction mixture. The amount of the lower molecular weight polyoxyethylene diol having an $M_n$ of about 600 to about 2,000 is about 1% to about 15%, and preferably from about 2% to about 10%, by weight, of the reaction mixture. Preferably, the alkylene glycol is diethylene glycol, cyclohexanedimethanol, dipropylene glycol, or a mixture thereof.

The 2,2-di-(hydroxymethyl)alkanoic acid preferably is dimethylolpropionic acid. The amount of dimethylolpropionic acid is about 1% to about 12%, preferably about 1.5% to about 8%, and most preferably about 2% to about 6% by weight of the reaction mixture. The final product has an acid value of at least about 0.2, and preferably at least about 1, mg KOH/g resin. To achieve the full advantage of the invention, the carboxylated polyurethane resin has an acid value of at least 7 mg KOH/g resin, e.g., about 7 to about 50 mg KOH/g resin.

Alternatively, an amine can be used in place of a portion of the water in the reaction mixture. An amount of about 0.15% to about 0.6% amine, based on diglycolamine, is used with about 0.06% to about 0.5% of water, more preferably about 0.1% to about 0.40% of water, and most preferably of about 0.15% to about 0.30% of water.

The carboxylated polyurethane resins of this embodiment are especially useful in hair spray compositions because the polyurethane resins are soluble in ethanol/water mixtures, and in dilute neutral to basic aqueous solutions, to form low viscosity solutions. Solutions of the polyurethane resins also exhibit improved sprayability, improved feel of sprayed hair, low flaking and crust, and improved set retention of the hair.

For hair spray compositions, the hydrophilicity of the polyurethane resin is an unexpected important property in combination with other desirable properties, such as washability. Conventional hair fixative resins are hydrophobic materials that impart a stiff feel to hair. The present carboxylated polyurethane resins are hydrophilic, which gives the hair a soft, natural feel, yet are adhesive to the hair and impart excellent hair set retention. It also has been found that the hair styling properties of the polyurethane resin can be effected by small changes in the amount of water, the NCO/OH ratio, and the amount of the di(hydroxymethyl) alkanoic acid in the reaction mixture.

For hair spray compositions, the preferred diol is a polyoxyethylene diol, preferably a polyoxyethylene diol of $M_n$ about 6000 to about 10,000, alternatively with about 1% to about 10% of polyoxyethylene diol of $M_n$ about 1000 to 2500. The water level is about 0.1% to about 0.5%, preferably about 0.15% to about 0.45%, and most preferably about 0.15% to about 0.4%.

A polyurethane resin having an $M_w$ of less than about 25,000 can be formed using a water level of about 0.25% to about 0.4% by weight of the reaction mixture, an NCO/OH ratio of about 0.55 to about 0.75, and a range of dimethylolpropionic acid of about 3.0% to about 6.5% by weight of the reaction mixture. The polyurethane resin has a kinematic viscosity at 3 wt. % in a 55/42 ethanol/water solution (by weight) of about 1 to about 20 cs. These polyurethane resins are useful as hair styling aids and forming low viscosity solutions in hair styling media.

It also has been found that polyurethane resins prepared using an amount of water of about 0.1% to about 0.4% by weight in the reaction mixture, and a NCO/OH ratio of about 0.55 to about 0.75, most preferably from about 0.57 to about 0.74, impart a crust value of about 3 to about 6, a set retention at 30 minutes and 75% relative humidity of about 75% to about 85%, and a set retention at 60 minutes and 75% relative humidity of about 55% to about 67%, to treated hair.

Alternatively, small amounts of diglycolamine can be substituted for water in the reaction mixture, e.g., about 0.02% to about 1%, preferably from about 0.03% to about 0.75%, more preferably from about 0.04% to about 0.5%, and most preferably from 0.05% to about 0.4% diglycolamine can be used in the reaction mixture.

The alkylene glycol used in this embodiment can be, for example, ethylene glycol, diethylene glycol, propylene glycol, dipropylene glycol, cyclohexanediol, 1,4-butanediol, cyclohexanedimethanol, tripropylene glycol, or triethylene glycol; preferably diethylene glycol, cyclohexanedimethanol, or dipropylene glycol; and most preferably diethylene glycol. The amount of the alkylene glycol (hard segments) in the reaction mixture is about 0.01% to about 20%, preferably about 0.05% to about 15%, more preferably about 0.1% to about 12%, still more preferably about 0.5% to about 10%, and most preferably about 1% to about 5%, by weight.

For hair spray compositions, the kinematic viscosity of a solution of the polyurethane resin having a 55/42/3 weight ratio of ethanol/water/polyurethane resin is less than about 50 centistokes (cs), preferably about 40 cs or less, and most preferably about 1 to about 25 cs.

In each embodiment, the polyurethane-forming reaction is catalyzed by known catalysts. Tin-containing catalysts, such as tin salts or organotin esters, for example, stannous octoate and dibutyltin dilaurate, or tertiary amines, such as triethylene diamine and N,N,N',N'-tetramethyl-1,3-butane diamine, are preferred. The catalyst is used in an amount effective to catalyze the reaction, i.e., about 0.001 to 1 weight percent of the total weight of the reaction mixture. Reaction temperature is about 40° C. to about 120° C.

In addition to the carboxylated polyurethane resin, the hair styling gel contains 0% to about 6%, and preferably about 0.25% to about 5%, by weight, of an optional second hair fixative resin. To achieve the full advantage of the present invention, the hair styling gel contains about 0.5% to about 4%, by weight of the composition of the optional second hair fixative resin. Preferably, the weight ratio of optional second hair fixative resin to carboxylated polyurethane resin in the composition is about one or less, i.e., 0 to about 1. The second hair fixative resin can be a nonionic, cationic, or anionic resin, because the carboxylated polyurethane resin is compatible with each class of resins. It also is envisioned that the optional second hair fixative resin is a mixture of two or more hair fixative resins in a total amount of 0% to about 6% by weight of the composition.

The optional second hair fixative resin preferably is a hydrophobic compound that retards the tendency of hair to absorb water. The second hair fixative resin also is a hard, brittle compound having a glass transition temperature (Tg) of about 100° C. or greater, e.g., up to 200° C., and preferably about 110° C. or greater, i.e., up to about 200° C. In contrast, the carboxylated polyurethane resin has a low Tg, i.e., less than 100° C., for example about 0° C. to about 50° C. An important feature of the optional second hair fixative resin is to reduce flaking attributed to the carboxylated polyurethane resins, and to impart properties to the hair typically associated with the second hair fixative resin, e.g., stiffness.

In particular, the optional second hair fixative resin can impart a desired and predetermined degree of stiffness to the hair. In contrast, the carboxylated polyurethane resin provides an elastic, flexible film on the hair, which gives the hair a natural feel. However, consumers often equate a good hair setting composition with a degree of hair stiffness. The present hair spray compositions, therefore, impart the desired stiffness to the hair, while further providing the benefits attributed to the polyurethane resin, such as conditioning, good style retention, and good hair feel.

Nonlimiting examples of second hair fixative resins useful in the present hair spray compositions can be found in Grollier et al. U.S. Pat. No. 4,445,521, incorporated herein by reference. Specific second hair fixative resins include, but are not limited to, acrylamide copolymers, acrylamide/sodium acrylate copolymer, acrylate/ammonium methacrylate copolymer, acrylate copolymers, acrylic/acrylate copolymers, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, ammonium acrylate copolymers, ammonium vinyl acetate/acrylate copolymers, AMP acrylate/diacetoneacrylamide copolymers, AMPD acrylate/diacetoneacrylamide copolymers, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine copolymer, dodecanedioic acid/cetearyl alcohol/glycol copolymer, ethyl ester of PVM/MA copolymer, isopropyl ester of PVM/MA copolymer, karaya gum, methacryloyl ethyl betaine/methacrylate copolymers, octylacrylamide/acrylate/butylaminoethyl methacrylate copolymers, octylacrylamide/acrylate copolymers, phthalic anhydride/glycerin/glycidyl decanoate copolymer, phthalic/trimellitic/glycol copolymers, polyacrylamide, polyacrylamidomethylpropane sulfonic acid, polybutylene terephthalate, polyethylacrylate, polyethylene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyvinyl acetate, polyvinyl butyral, polyvinyl imidazolinium acetate, polyvinyl methyl ether, PVM/MA copolymer, PVP, PVP/dimethylaminoethylmethacrylate copolymer, PVP/eicosene copolymer, PVP/ethyl methacrylate/methacrylic acid copolymer, PVP/hexadecene copolymer, PVP/VA copolymer, PVP/vinyl acetate/itaconic acid copolymer, shellac, sodium acrylate/vinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, vinyl acetate/crotonate copolymers, vinyl acetate/crotonic acid copolymer, vinyl acetate/crotonic acid/methacryloxybenzophenone-1 copolymer, vinyl acetate/crotonic acid/vinyl neodecanoate copolymer, and mixtures thereof.

In addition to the carboxylated polyurethane resin and the optional second hair fixative resin, the hair spray composition contains 0% to about 80%, by total weight of the composition, of an alcohol. Preferably, the composition contains 0% to about 55%, by weight, of an alcohol. In order to reduce the adverse environmental affects attributed to volatile organic compounds, the amount of alcohol is maintained at as low a level as possible without adversely affecting the esthetics or efficacy of the hair spray composition.

The alcohol typically used in the hair spray composition is ethanol, although isopropyl alcohol also can be incorporated into the composition. The carboxylated polyurethane resins are readily solubilized in a wide range of hydroalcoholic solutions, without the addition of basic neutralizer, thereby permitting a decrease in the amount of alcohol present in the hair spray composition.

The hair spray composition also contains 15% to about 99%, by total weight of the composition, of water. The amount of water is maximized in order to reduce the amount of VOC in the composition. Because the carboxylated polyurethane resins are hydrophilic, it is not necessary to include a base in the water to neutralize and solubilize the polyurethane resin.

Optional ingredients also can be incorporated into the hair spray compositions. The identity of the optional ingredients is not limited as long as the optional ingredients do not adversely affect the esthetics or efficacy of the hair spray composition. For example, a hair spray composition containing only a carboxylated polyurethane resin, water, and alcohol can be applied as a nonaerosol pump spray. The composition can be modified for application as an aerosol spray by incorporating about 5% to about 30%, by weight of the composition, of a propellant. The carboxylated polyurethane resin tolerates the propellant gases commonly used in aerosol compositions, such as the alkanes and carbon dioxide.

The optional propellant gas included in the hair spray compositions can be any liquefiable gas conventionally used for aerosol products. Examples of compounds that are suitable for use as propellants are trichlorofluoromethane, dichlorodifluoromethane, dichlorotetraf luoroethare, monochlorodif luoromethane, trichlorotrifluoroethane, dimethyl ether, propane, n-butane, and isobutane, either singly or admixed. Water-soluble gases such as dimethyl ether, carbon dioxide, and/or nitrous oxide also can be used to obtain aerosol sprays having reduced flammability.

Water-immiscible, liquified, hydrocarbon and halogenated hydrocarbon gases such as propane, butane, and chlorofluorocarbons can be used advantageously to deliver the contents of an aerosol container without the dramatic pressure drops associated with other immiscible gases. The head space left inside the aerosol container is not a factor because the liquified gas sits on top of the aqueous composition and the pressure inside the container is maintained at the vapor pressure of the saturated hydrocarbon vapor.

Other insoluble, compressed gases such as nitrogen, helium, and fully fluorinated oxetanes and oxepanes also are useful to deliver the compositions from aerosol containers. If the propellant, such as dimethyl ether, incorporates a vapor pressure suppressant (e.g., trichloroethane or dichloromethane), the amount of suppressant is included as part of the propellant for weight percentage calculations.

The hair spray compositions also can contain a variety of other nonessential, optional components. Such conventional optional ingredients are well known to those skilled in the art, e.g., emulsifiers, such as anionic or nonionic surfactants; preservatives, such as benzyl alcohol, methyl paraben, propyl paraben, or imidazolidinylurea; cationic conditioners, such as cetyl trimethyl ammonium chloride, stearyl dimethyl benzyl ammonium chloride, and di(partially hydrogenated tallow) dimethyl ammonium chloride; coloring agents, such as any of the FD&C or D&C dyes; perfume oils; and chelating agents, such as ethylenediaminetetraacetic acid. These optional materials generally are included individually at a level of 0% to about 5%, by weight of the total composition.

The aqueous formulations of the present invention also can contain conventional hair spray adjuvants in amounts 0% to about 2% by weight, and preferably 0% to about 1% by weight. Among the additives which can be used are plasticizers, such as glycols, phthalate esters, and glycerin, silicones, emollients, lubricants, and penetrants, such as various lanolin compounds, protein hydrolysates, and other protein derivatives, ethylene adducts and polyoxyethylene cholesterol.

The hair spray compositions of the present invention are prepared by simply admixing and dissolving the polyurethane resin and any optional ingredients into an aqueous or hydroalcoholic carrier. The resulting solution can be used as is in a pump spray, or can be pressurized by the addition of an aerosol propellant in accordance with methods well known in the art.

POLYMER PREPARATION

Polyurethane Resin A

Polyoxyethylene diol having a number average molecular weight ($M_n$) of 8000 was heated under vacuum to 0.215% of water, and 736 parts of the dried diol was added to 21 parts of diethylene glycol, 59 parts of dimethylolpropionic acid, and 1.81 parts of water. The mixture was heated with stirring until a homogeneous melt was obtained. Then, 168 parts of methylene bis-cyclohexyl-4-4'-diisocyanate were added. The NCO/OH ratio was 0.65. When the temperature reached about 70° C., 1.85 ml of dibutyltin dilaurate was added, a n d the mass was allowed to exotherm. The mass was heated at 100° C. for about one hour to complete formation of the polyurethane resin. The polyurethane resin had a weight average molecular weight ($M_w$) of 15,000 and dissolved in slightly basic 55/45 ethanol/water (wt/wt) solution at a concentration of 5 wt. % was clear and had a viscosity of 10 cps. The polyurethane resin had a kinematic viscosity of 4.60 cps in 55/42/3 ethanol/water/polymer solution by weight. The polyurethane resin was used in a hair styling aid to impart superior soft feel, excellent set retention, low crust, and low flaking properties to hair. Hair treated with the polyurethane resin had a crust rating of 4.5, a feel of 4.5, a flaking rating of 1.8, a set retention of 85% at 30 minutes.

Polyurethane Resin B

Polyoxyethylene diol having an $M_n$ of 8000 was heated under vacuum to 0.156% of water and 756 parts of the dried diol was added to 21 parts of diethylene glycol, 39 parts of dimethylolpropionic acid, and 0.25 part of water. The mixture was heated with stirring until a homogeneous melt was obtained. Then, 136 parts of methylene bis-cyclohexyl-4-4'-diisocyanate were added. The NCO/OH ratio was 0.75. When the temperature reached about 66° C., 1.85 ml of dibutyltin dilaurate was added, and the mass was allowed to exotherm. The mass was heated at 100° C. for about one hour to complete formation of the polymer. The polyurethane resin dissolved in a slightly basic 55/45 ethanol/water solution (wt/wt) at a concentration of 5 wt. % to produce a clear solution with a viscosity of 11 cps. The polyurethane resin was used in a hair styling aid to impart superior soft feel, excellent set retention, low crust, and low flaking properties to hair. Hair treated with the polyurethane resin had a crust rating of 6.9, a feel of 5.5, a set retention of 95% at 30 minutes, and a set retention of 90% at 60 minutes.

Comparative Polyurethane Resin C

Polyoxyethylene diol having an $M_n$ of 8000 was heated under vacuum to 0.032% of water and 736 of the dried diol was added to 21 parts of diethylene glycol, 18 parts of dimethylolpropionic acid, and 2.06 parts of water. The mixture was heated with stirring until a homogeneous melt was obtained. Then, 113 parts of methylene bis-cyclohexyl-4-4'-diisocyanate were added. The NCO/OH ratio was 0.75. When the temperature reached about 65° C., 1.85 ml of dibutyltin dilaurate was added, and the mass was allowed to exotherm. The mass was heated at 100® C. for about one hour to complete formation of the polymer. The polymer dissolved in a slightly basic 55/45 ethanol/water solution (wt/wt) at a concentration of 5 wt. % to produce a clear solution with a viscosity of 13 cps. The polyurethane resin had a kinematic viscosity of 6.5 cs in 55/42/3 ethanol/water/polymer by weight solution. The polyurethane resin was used to make a hair styling aid. The polyurethane resin imparted a crust rating of 4.2, a feel of 4.8, a flaking rating of 4.2, a set retention of 86% at 30 minutes and a set retention of 73% at 60 minutes to treated hair.

Comparative Polyurthane Resin D

Polyoxyethylene diol having an $M_n$ of 8000 was heated under vacuum to 0.060% of water and 736 parts of the dried diol was added to 21 parts of diethylene glycol, 18 parts of dimethylolpropionic acid, and 2.84 parts of water. The mixture was heated with stirring until a homogeneous melt was obtained. Then, 139 parts of methylene bis-cyclohexyl-4-4'-diisocyanate were added. The NCO/OH ratio was 0.85. When the temperature reached about 64° C., 1.85 ml of dibutyltin dilaurate was added, and the mass was allowed to exotherm. The mass was heated at 100° C. for about one hour to complete formation of the polymer. The polyurethane resin had an $M_w$ of 76,000 and dissolved in a slightly basic 55/45 ethanol/water solution (wt/wt) at a concentration of 5 wt. % to give a viscosity of 18 cps. The polyurethane resin had a kinematic viscosity of 14.7 cs in 55/42/3 ethanol/water/polymer solution by weight. The polyurethane resin was used to make a hair styling aid.

Polyurethane Resin E

Polyoxyethylene diol having an $M_n$ of 8000 was heated under vacuum to 0.074% of water and 281 parts added to 7.9 parts of diethylene glycol, 55 parts of dimethylolpropionic acid, and 1.38 parts of water. The mixture was heated with stirring until a homogeneous melt was obtained. Then, 109 parts of methylene bis-cyclohexyl-4-4 '-diisocyanate were added. The NCO/OH ratio was 0.65. When the temperature reached about 70° C., 0.68 ml of dibutyltin dilaurate was added, and the mass was allowed to exotherm. The mass was heated at 100° C. for about one hour to complete formation of the polymer. The polyurethane resin dissolved in a slightly basic 55/45 ethanol/water solution (wt/wt) at a concentration of 5 wt. % to produce a clear solution having a viscosity of 10 cps.

Polyurethane Resin F

Polyoxyethylene diol having an $M_n$ of 8000 was heated under vacuum to 0.099% of water and 306 parts of the dried diol was added to 34 parts of a block copolymer of ethylene oxide and propylene oxide made by BASF under the tradename of F127, 9.5 parts of diethylene glycol, 27 parts of dimethylolpropionic acid, and 1.30 parts of water. The mixture was heated with stirring until a homogeneous melt was obtained. Then, 77 parts of methylene bis-cyclohexyl-4-4'-diisocyanate were added. The NCO/OH ratio was 0.65. When the temperature reached about 67° C., 0.68 ml of dibutyltin dilaurate was added, and the mass was allowed to exotherm. The mass was heated at 100° C. for about one hour to complete formation of the polyurethane resin. The polyurethane resin can be dissolved in slightly basic 55/45 ethanol/water (wt/wt) at a concentration of 5 wt. % to produce a clear solution having a viscosity of less than 20 cps.

Comparative Polyurethane Resin G

Polyoxyethylene diol having an $M_n$ of 8000 was heated under vacuum to 0.061% of water, and 736 parts of the dried diol was added to 21 parts of diethylene glycol, 59 parts of dimethylolpropionic acid, and 1.11 part of water. The mixture was heated with stirring until a homogeneous melt was obtained. Then, 185 parts of methylene bis-cyclohexyl-4-4'-diisocyanate were added. The NCO/OH ratio was 0.85. When the temperature reached about 63° C., 1.85 ml of dibutyltin dilaurate was added, and the mass was allowed to exotherm. The mass was heated at 100° C. for about one hour to complete formation of the polymer. The polyurethane resin had an $M_w$ of 21,000 and dissolved in slightly basic 55/45 ethanol/water solution (wt/wt) at a concentration of 5 wt. % was clear and had a viscosity of 10 cps. The polyurethane resin had a kinematic viscosity of 6.15 cs in 55/42/3 ethanol/water/polymer solution by weight. The polyurethane resin was used to prepare a hair styling aid.

Comparative Polyurethane Resin H

Polyoxyethylene diol having an $M_n$ of 8000 was heated under vacuum to 0.060% of water, and 736 parts of the dried diol was added to 21 parts of diethylene glycol, 18 parts of dimethylolpropionic acid, and 0.96 part of water. The mixture was heated with stirring until a homogeneous melt was obtained. Then, 114 parts of methylene bis-cyclohexyl-4-4'-diisocyanate were added. The NCO/OH ratio was 0.85. When the temperature reached about 63° C., 1.85 ml of dibutyltin dilaurate was added, and the mass was allowed to exotherm. The mass was heated at 100° C. for about one hour to complete formation of the polyurethane resin. The polyurethane resin dissolved in slightly basic 55/45 ethanol/water solution (wt/wt) at a concentration of 5 wt. % was clear and had a viscosity of 14 cps. The polyurethane resin had an $M_w$ of 40,000 and was used in a hair styling aid.

Comparative Polyurethane Resin I

Polyoxyethylene diol having an $M_n$ of 8000 was heated under vacuum to 0.060% of water, and 336 parts of the dried diol was added to 9.3 parts of diethylene glycol, 27 parts of dimethylolpropionic acid, 8.2 parts of diglycolamine and 0.002 part of water. The mixture was heated with stirring until a homogeneous melt was obtained. Then, 73 parts of methylene bis-cyclohexyl-4-4'-diisocyanate were added. The NCO/OH ratio was 0.65. When the temperature reached about 65° C., 0.92 ml of dibutyltin dilaurate was added, and the mass was allowed to exotherm. The mass was heated at 100° C. for about one hour to complete formation of the polymer. The polyurethane resin dissolved in slightly basic 55/45 ethanol/water solution (wt/wt) at a concentration of 5 wt. % was clear. The polyurethane resin had a kinematic viscosity of 5.93 cs in 55/42/3 ethanol/water/polymer solution by weight.

Polyurethane Resin J

Polyoxyethylene diol having an $M_n$ Of 8000 and polyoxyethylene diol having an $M_n$ of 1450 were heated under vacuum to 0.132% of water, and 291 parts of the higher molecular weight dried diol and 15.3 parts of lower molecular weight dried diol were added to 9.5 parts of dipropylene glycol, 27 parts of dimethylolpropionic acid, 34 parts of polyoxypropylene glycol of 425 molecular weight, and 1.146 part of water. The mixture was heated with stirring until a homogeneous melt was obtained. Then, 89 parts of methylene bis-cyclohexyl-4-4'-diisocyanate were added. The NCO/OH ratio was 0.65. When the temperature reached about 67° C., 0.68 ml of dibutyltin dilaurate was added, and the mass was allowed to exotherm. The mass was heated at 100° C. for about one hour to complete formation of the polymer. The polyurethane resin dissolved in slightly basic 55/45 ethanol/water solution (wt/wt) at a concentration of 5 wt. % was clear, and had a viscosity of 8 cps. The polyurethane resin was used in a hair spray composition to give treated hair a superior soft feel, excellent set retention, low crust, and low flaking properties.

An important property of a hair spray composition is the ability to wash the hair setting resin from the hair, and thereby avoid polymer buildup on the hair. In accordance with an important feature of the present invention, a carboxylated polyurethane resin used in the hair spray composition can be removed from the hair by simply shampooing the hair. The unexpected washability of the hair spray composition is attributed to the hydrophilic nature of the polyurethane resin, and especially to the acid value of the carboxylated polyurethane resin. When the acid value of the resin is at least about 7 mg KOH/g of resin, the polyurethane resin can be rinsed from the hair during shampooing without the need to neutralize the resin with an organic base.

The acid value is an indication of the number of pendant carboxylic acid groups on the polyurethane resin backbone. Although noncarboxylated polyurethane resins are hydrophilic, they are difficult to wash from the hair in a short time. Washability is enhanced by incorporating pendant carboxylic acid groups onto the polyurethane backbone.

The effect of acid value is illustrated in Tables 1 and 2, wherein it is shown that washability is independent of $M_w$ or R-value, but varies with acid value. In effect, carboxylated polyurethane resins having an acid value of about 7 mg KOH/g of resin or greater, i.e., about 7 to about 50 mg KOH/g resin, had improved washability over resins having an acid value less than 7 mg KOH/g resin.

TABLE 1

PROPERTIES OF POLYURETHANE RESINS
(R-VALUE = 0.73 TO 0.98)

| Polyurethane Resin | R-value | Water | Acid Value[1] | Molecular Weight[2] | PDI[3] | Washability[4] |
|---|---|---|---|---|---|---|
| 1 | 0.98 | low | 0.42 | 174,000 | 2.00 | no |
| 2 | 0.98 | low | 2.28 | 141,000 | 2.00 | no |
| 3 | 0.84 | low | 8.01 | 28,000 | 2.00 | yes |
| 4 | 0.93 | low | 7.88 | 37,000 | 2.00 | yes |
| 5 | 0.98 | low | 8.28 | 63,000 | 2.00 | yes |
| 6 | 0.98 | medium | 0.50 | 188,000 | 2.20 | no |
| 7 | 0.85 | medium | 2.47 | 64,000 | 1.90 | no |
| 8 | 0.85 | medium | 8.62 | 37,000 | 1.70 | yes |
| 9 | 0.88 | medium | 7.87 | 30,000 | 1.60 | yes |
| 10 | 0.90 | medium | 7.70 | 43,000 | 1.80 | yes |
| 11 | 0.90 | medium | 8.04 | 39,000 | 1.70 | yes |
| 12 | 0.94 | medium | 7.78 | 39,000 | 1.80 | yes |
| 13 | 0.85 | high | 7.91 | 38,000 | 1.80 | yes |
| 14 | 0.90 | high | 7.70 | 46,000 | 1.90 | yes |
| 15 | 0.73 | low | 15.19 | 23,000 | na | yes |
| 16 | 0.73 | low | 7.10 | 59,000 | na | yes |
| 17 | 0.98 | low | 3.66 | 117,000 | na | no |
| 18 | 0.98 | low | 4.03 | 85,000 | na | no |

[1]The acid value was measured by titrating a solution of the resin with potassium hydroxide, the acid value is expressed in milligrams of KOH per gram of polyurethane resin;
[2]The molecular weight is the weight average molecular weight ($M_w$) measured by size exclusion chromatography using polyethylene glycol calibration standards;
[3]PDI is an abbreviation for "polydispersity index," i.e., the ratio [Weight average molecular weight]/[Number average molecular weight], which measures the relative spread in the molecular weight of the polyurethane resin; and
[4]The washability of the resin was determined by applying 3 wt. % solution of polyurethane resin onto clean, 2 gram, 6-inch long hair tresses, allowing the hair to dry, then washing the hair tresses with shampoo and warm water for about 3 minutes.

TABLE 2

PROPERTIES OF POLYURETHANE RESINS
(R-VALUE = 0.65 TO 0.85)

| Polyurethane Resin | R-value | Water | Acid Value[1] | Molecular Weight[2] | Washability[4] |
|---|---|---|---|---|---|
| 19 | 0.75 | med | 16.30 | 18,000 | yes |
| 20[5] | 0.65 | high | 8.22 | 26,000 | yes |
| 21 | 0.65 | med | 17.02 | 16,000 | yes |
| 22[6] | 0.85 | low | 23.31 | 21,000 | yes |
| 23[7] | 0.75 | high | 22.48 | 24,000 | yes |
| 24[8] | 0.85 | high | 7.75 | 76,000 | yes |
| 25 | 0.65 | high | 16.53 | 15,000 | yes |

TABLE 2-continued

PROPERTIES OF POLYURETHANE RESINS
(R-VALUE = 0.65 TO 0.85)

| Polyurethane Resin | R-value | Water | Acid Value[1] | Molecular Weight[2] | Washability[4] |
|---|---|---|---|---|---|
| 26[9] | 0.65 | high | 24.22 | 15,000 | yes |
| 27 | 0.85 | med | 16.37 | 27,000 | yes |
| 28 | 0.75 | low | 16.45 | 25,000 | yes |
| 29[10] | 0.75 | med | 8.11 | 35,000 | yes |
| 30[11] | 0.85 | low | 8.01 | 40,000 | yes |

[5]Comparative Polyurethane Resin I;
[6]Comparative Polyurethane Resin G;
[7]Polyurethane Resin B;
[8]Comparative Polyurethane Resin D;
[9]Polyurethane Resin A;
[10]Comparative Polyurethane Resin C; and
[11]Comparative Polyurethane Resin H.

A hair spray composition of the present invention also can be evenly delivered as a spray. In particular, the carboxylated polyurethane resins are suitable for preparing hair spray compositions containing various levels of volatile organic compounds (VOC). Hair spray compositions containing 55% VOC and having food spray properties have a viscosity of about 1 to about 10 cps. Hair spray compositions containing 80% Voc and having good spray properties have a viscosity of about 1 to about 25 cps. Accordingly, it was found that to provide a hair spray composition having excellent spray characteristics, the $M_w$ of the carboxylated polyurethane resin is about 10,000 to about 25,000, and preferably about 13,000 to about 24,000.

Aerosol and nonaerosol hair spray compositions of the present invention were prepared by dissolving 5%, by weight, of a carboxylated polyurethane resin in a blend of water and ethanol, then pouring the resulting solution into an aerosol can. The filled can was crimped with a conventional aerosol valve. Then, 30 weight % dimethyl ether (i.e., DME), was charged into the aerosol can. Nonaerosol, pump hair spray compositions are prepared by simply dissolving the polyurethane resin in a water/ethanol blend. Examples of hair spray compositions are generally set forth below:

| Aerosol Hair Spray (55% VOC) | |
|---|---|
| Polyurethane resin | 5 (% wt.) |
| Ethanol | 25 |
| DME | 30 |
| Water | 40 |

| Aerosol Hair Spray (80% VOC) | |
|---|---|
| Polyurethane resin | 5 (% wt.) |
| Ethanol | 50 |
| DME | 30 |
| Water | 15 |

| Pump Hair Spray (80% VOC) | |
|---|---|
| Polyurethane resin | 5 (% wt.) |
| Ethanol | 80 |
| Water | 15 |

| Pump Hair Spray (55% VOC) | | |
|---|---|---|
| | a | b |
| Polyurethane resin | 5 (% wt.) | 3 (% wt) |
| Ethanol | 55 | 55 |
| Water | 40 | 42 |

The results summarized in Tables 3 through 5 show that the present hair spray compositions containing a carboxylated polyurethane resin having an R-value of about 0.55 to about 0.75 and an $M_w$ of about 10,000 to about 25,000 can be applied to the hair as an aerosol spray or a pump spray. The results also illustrate that sprayability of the hair spray composition, set retention, feel, flaking, and crust formation are optimized when the carboxylated polyurethane resin has an R-value of about 0.57 to about 0.74, and an $M_w$ of about 13,000 to about 24,000.

TABLE 3

PROPERTIES OF THE CARBOXYLATED POLYURETHANE RESINS

| Polyurethane Resin | Water Level | R-Value | Acid Level (%)[12] | $M_w$ | $M_z$ | Viscosity (cs) 3% sol.[13] | Viscosity (cs) 5% sol.[13] |
|---|---|---|---|---|---|---|---|
| 31 | med | 0.75 | 4 | 18K | 28K[14] | 5.03 | 7.73 |
| 32 | low | 0.65 | 2 | 19K | 28K | 5.06 | 7.64 |
| 20[5] | high | 0.65 | 2 | 26K | 43K | 5.84 | 9.95 |
| 33 | med | 0.65 | 4 | 16K | 26K | 4.28 | 7.47 |
| 22[6] | low | 0.85 | 6 | 21K | 35K | 6.15 | 10.03 |
| 23[7] | high | 0.85 | 6 | 24K | 42K | 5.92 | 10.79 |
| 24[8] | high | 0.85 | 2 | 76K | 148K | 14.71 | 20.74 |
| 34 | high | 0.75 | 4 | 20K | 32K | 5.69 | 9.25 |
| 35 | med | 0.75 | 6 | 18K | 28K | 5.00 | 8.26 |
| 25 | high | 0.65 | 6 | 15K | 23K | 4.60 | 7.05 |
| 29[10] | med | 0.85 | 4 | 27K | 48K | 6.28 | 12.47 |
| 36 | low | 0.75 | 4 | 25K | 40K | 5.90 | 10.58 |
| 37 | med | 0.75 | 2 | 35K | 58K | 6.59 | 10.85 |
| 38 | low | 0.65 | 6 | 15K | 23K | 4.54 | 6.54 |
| 30[11] | low | 0.85 | 2 | 40K | 70K | 7.82 | 13.15 |
| 39 | med | 0.75 | 4 | 18K | 28K | 5.03 | 7.73 |
| 40 | higher | 0.65 | 4 | 19K | 29K | 5.03 | 7.70 |
| 41 | higher | 0.65 | 4 | 16K | 25K | 4.83 | 7.52 |

TABLE 3-continued

PROPERTIES OF THE CARBOXYLATED POLYURETHANE RESINS

| Polyurethane Resin | Water Level | R-Value | Acid Level (%)[12] | $M_w$ | $M_z$ | Viscosity (cs) 3% sol.[13] | 5% sol.[13] |
|---|---|---|---|---|---|---|---|
| 42 | highest | 0.65 | 6 | 20K | 32K | 5.24 | 8.45 |
| 43 | highest | 0.55 | 4 | 17K | 25K | 4.67 | 6.90 |

[12]An acid level of 2% to 6% corresponds to an acid value of about 7 to about 50 mg KOH/g resin;
[13]weight percent of carboxylated polyurethane resin in solution; and
[14]K = 1000.

TABLE 4

SPRAY PROPERTIES OF A HAIR SPRAY COMPOSITION

| Polyurethane Resin | Spray Pattern[15] 3% sol.[13] | 5% sol.[13] |
|---|---|---|
| 31 | 2[16] | 2 |
| 32 | 1 | 2 |
| 20[5] | 1 | 3 |
| 33 | 1 | 2 |
| 22[6] | 2 | 4 |
| 23[7] | 2 | 4 |
| 24[8] | 4 | 4 |
| 34 | 2 | 2 |
| 35 | 1 | 2 |
| 25 | 1 | 1 |
| 29[10] | 3 | 4 |
| 36 | 1 | 3 |
| 37 | 1 | 4 |
| 38 | 1 | 1 |
| 30[11] | 4 | 4 |
| 39 | 2 | 2 |
| 40 | 1 | 2 |
| 41 | 1 | 1 |
| 42 | 1 | 2 |
| 43 | 1 | 2 |

[15]The spray pattern of the aerosol formulations was evaluated visually. A standard spray can with an actuator button having orifice diameter of 0.018 inch was used. The hair spray composition was sprayed in the air for about 10 seconds. A very bad or a bad spray pattern occurs when the composition sputters when leaving the actuator, the spray particles are too large or coarse (i.e., particle average diameter greater than 200 microns), the composition foamsor clogs the actuator, or the spray cross section is narrow (i.e., less than 2 inches diameter). A marginal spray pattern is somewhat coarse, having an average particle diameter between 100 to 150 microns. A good spray pattern is when the spray leaves the can smoothly without sputtering or clogging, the spray particle size is fine, the particle average diameter is less than 100 microns, and there is no foaming; and
[16]Rating Scale: Acceptable: 1 = excellent, 2 = good; Unacceptable: 3 = marginal, 4 = bad.

An analysis of the properties of the carboxylated polyurethane listed in Table 3 and used in the spray pattern experiments summarized in Table 4 showed that the R-value and the $M_w$ had the most significant effects on the spray pattern. As shown in detail hereafter, a carboxylated polyurethane resin having an R-value of about 0.55 to about 0.75, and an $M_w$ of about 10,000 to about 25,000 (i.e., an $M_z$ of about 20,000 to about 40,000) provided the best spray results, and imparted a good hair set retention and feel to sprayed hair.

In particular, Table 4 shows that Polyurethane Resins 22–24, 29, 30, 36, and 37, each having an R-value of about 0.85 and an $M_w$ of about 21,000 to about 76,000 exhibited an unacceptable spray pattern rated 4, i.e., bad, for a 3% and/or a 5% solution of the carboxylated polyurethane resin, by weight. Polyurethane Resin 20, having an R-value of 0.65 and an $M_w$ of about 26,000, exhibited a marginal spray pattern for a 5% solution of carboxylated polyurethane resin, by weight. Polyurethane Resins 25, 36, and 38–43, each having an R-value of about 0.55 to about 0.75 and an $M_w$ of about 10,000 to about 25,000, demonstrated acceptable spray problems, and typically demonstrated excellent spray patterns.

TABLE 5

PERFORMANCE EVALUATION (AVERAGE RATINGS)

| Polyurethane Resin (Acceptable Ratings) | Crust (3–6) | Feel (≤5) | Flaking (≤4) | Hair Set (30 min.) (80% ± 10) | Hair Set (60 min.) (65% ± 10) |
|---|---|---|---|---|---|
| 31 | 4.77 | 5.02 | 2.92 | 77.68 | 65.43 |
| 32[18, 21] | 2.25 | 2.04 | 1.16 | 54.10 | 37.50 |
| 20[5, 17] | 4.28 | 4.80 | 3.75 | 74.06 | 55.97 |
| 33[21] | 3.03 | 2.68 | 1.65 | 52.77 | 46.07 |
| 22[6, 17–20] | 6.29 | 8.14 | 8.34 | 81.20 | 68.52 |
| 23[7, 17–20] | 6.92 | 8.35 | 7.05 | 94.56 | 89.80 |
| 24[8, 17–20] | 8.29 | 9.56 | 8.43 | 94.19 | 91.40 |
| 34[17–21] | 6.51 | 7.23 | 5.71 | 82.76 | 70.42 |
| 35[19, 20] | 4.82 | 5.63 | 5.06 | 65.76 | 49.45 |
| 25 | 4.50 | 4.54 | 1.82 | 85.34 | 63.24 |
| 29[10, 17–20] | 6.39 | 8.20 | 7.18 | 94.19 | 80.00 |
| 36[17, 19, 20] | 5.53 | 6.41 | 6.69 | 89.17 | 75.37 |
| 37[17] | 4.21 | 4.84 | 4.22 | 85.68 | 72.98 |
| 38[18, 21] | 2.58 | 3.10 | 2.50 | 47.16 | 36.36 |
| 30[11, 17, 19, 20] | 4.88 | 6.72 | 7.03 | 96.76 | 95.13 |
| 39 | 4.40 | 1.54 | 1.68 | 81.41 | 67.12 |
| 40 | 2.80 | 2.10 | 1.30 | 74.16 | 56.01 |
| 41 | 3.70 | 2.25 | 1.44 | 81.35 | 66.67 |
| 42[21] | 4.00 | 1.32 | 0.94 | 63.72 | 43.54 |
| 43[18, 21] | 2.70 | 1.02 | 1.25 | 38.29 | 29.11 |

[17]Unacceptable spray pattern;
[18]Crust outside range;
[19]Feel above range;
[20]Flaking above range;
[21]Low set retention; and
[22]At 25° C. and 85% relative humidity.

Hair sprayed with a carboxylated polyurethane resin was rated by the trained panelists on a scale of 1 (best) to 10 (worst). The ten individual ratings were averaged and are set forth in Table 5. With respect to hair feel, a good feel has a rating of 5 or less. The sprayed hair was evaluated for degree of raspiness, coating, and gluing by rubbing a treated hair tress between the fingers. Crust or stiffness is evaluated by compressing a treated tress between the fingers. Hair having a soft, natural feel has a rating of 3 to 6. A low amount of flaking has a rating of 4 or less. Flaking was evaluated by combing a treated, dried hair tress three times, and the amount of flakes was recorded visually. The acceptable ranges for hair feel, crust, and flaking are those exhibited by current commercial products, and, consequently, are preferred, or at least accepted, by consumers, i.e., are exhibited by a consumer-acceptable hair spray.

The data summarized in Table 5 shows that hair spray compositions containing a carboxylated polyurethane resin having an R-value of about 0.55 to about 0.75, and an $M_w$ of about 10,000 to about 25,000, exhibited an acceptable spray pattern, provided a good hair set retention and feel, and exhibited a low crust and low flaking. In particular, Polyurethane Resins 25, 31, and 39–41 have an R-value and an $M_w$ within these ranges and effectively treat the hair. Polyurethane Resin 20 ($M_w$ of 26,000) had a marginal spray pattern thereby showing that a carboxylated polyurethane resin having an $M_w$ of 25,000 provides sprayed hair having consumer-acceptable properties. Polyurethane Resin 37, having an $M_w$ of 35,000, similarly showed a poor spray pattern. The carboxylated polyurethane resin requires an $M_w$ of at least 10,000 in order to sufficiently retain the hair set.

Polyurethane Resin 22 had an $M_w$ of 21,000 and an R-value of 0.85. However, hair treated with a hair spray composition containing Polyurethane Resin 22 had an unacceptable spray pattern, and an unacceptable crust, flaking, and feel. Therefore, in addition to an $M_w$ of about 15,000 to about 25,000, the polyurethane resin requires an R-value of about 0.55 to about 0.75, as shown by Polyurethane Resins 25, 31, and 39–41.

The data summarized in Tables 3 through 5 also show that the best hair set retention is achieved when the hair is treated with a carboxylated polyurethane resin having an R-value of about 0.63 to about 0.75. Therefore, to achieve the full advantage of the present invention, the carboxylated polyurethane resin has an R-value of about 0.63 to about 0.74.

In particular, the set retention test measures the ability of a hair spray composition to hold or retain a hair style for an extended time at a particular relative humidity. Set retention was measured by applying 0.5 cc (cubic centimeters) of the hair spray composition to a one gram hair tress, and testing six tresses per composition. The sprayed tresses were allowed to dry overnight, at 30% relative humidity (i.e., RH), in a zigzag shape. The tresses were hung inside a humidity chamber at 25° C. and a predetermined relative humidity (e.g., 70% RH). The relaxed length was recorded of the tresses and set retention was calculated using the equation:

$$\% \text{ Set Retention} = \frac{L - L_t}{L - L_o} \times 100,$$

wherein L is the length of the fully extended tress, $L_o$ is the length of sprayed hair before relaxation, $L_t$ is the length after exposure for a time, t. Six tresses were tested per hair spray composition and the data was statistically analyzed and compared at the 95% confidence level. In all comparative experiments, AMPHOMER was used as the resin in a control hair spray product.

Hair set retention was measured at a low relative humidity (i.e., 70% RH) and at a high relative humidity (i.e., 85% RH) at 25° C. Table 6 summarizes further hair set retention tests, and hair crust tests, from hair spray compositions incorporating various carboxylated polyurethane resins. The hair set retention and hair crust test results were compared to the results provided by a control hair spray product containing AMPHOMER. The comparative test shows that hair spray compositions containing a carboxylated polyurethane resin having an $M_w$ of about 10,000 to about 25,000, exhibited a set retention comparable to AMPHOMER. The hair set retention provided by such carboxylated polyurethane resins, therefore, is considered to be excellent because AMPHOMER is the hair fixative resin used in successful commercial hair spray compositions.

TABLE 6

| Polyurethane Resin | Stiffness and Crust[23] | Feel[24] | Flaking[25] | % Set Retention 1 hr. @ 85% RH |
|---|---|---|---|---|
| 19 | 4.77 | 5.02 | 2.92 | 65.43 |
| 20[5] | 4.28 | 4.80 | 3.75 | 55.97 |
| 21 | 3.03 | 2.68 | 1.65 | 46.07 |
| 22[6] | 6.29 | 8.14 | 8.34 | 68.52 |
| 23[7] | 6.92 | 8.35 | 7.05 | 89.80 |
| 24[8] | 8.29 | 9.56 | 8.43 | 91.40 |
| 25 | 6.51 | 7.23 | 5.71 | 70.42 |
| 26[9] | 4.50 | 4.54 | 1.82 | 63.24 |
| 27 | 6.39 | 8.20 | 7.18 | 80.00 |
| 28 | 5.53 | 6.51 | 6.69 | 75.37 |
| 29[10] | 4.21 | 4.48 | 4.22 | 72.98 |
| 30[11] | 4.88 | 6.72 | 7.03 | 95.13 |
| Control[26] | 7.00 | 7.00 | 6.00 | 62.50 |

[23]Two-inch wide, 6-inch long, 2 gram, clean hair tresses were treated with a hair spray composition. Six tresses were tested for each composition. The tresses were allowed to dry and evaluated for stiffness and crust with the fingers by trained judges using a scale: 1 to 10 (1 = soft and natural, 10 very stiff);
[24]The evaluation protocol is similar to the one described in footnote 23 on a scale: 1 to 10 (1 = untreated hair, 10 = coated and glued hair);
[25]The evaluation protocol is similar to the one described in footnote 23. However, instead of feeling the tresses, the tresses were combed and the amount and quality of the resin detached from the hair was visually evaluated by the trained judges; and
[26]The control was octylacrylamide/acrylates/butylaminoethyl/methacrylate copolymer, available as AMPROMER, from National Starch and Chemical Corp., Bridgewater, NJ.

Sprayed hair also was further tested for hair crust, feel, and flaking by comparison to a control resin. The hair crust test measures the hardness and/or stiffness of hair sprayed with a hair spray composition. Hair spray compositions that provide natural, or reduced, crusts are desired.

Hair crust was tested subjectively. In this test, a group of trained Judges evaluated hair tresses sprayed with a hair spray composition containing a polyurethane resin or with the control composition. The data and test procedure are summarized in Table 6. Table 6 shows the present hair spray compositions displayed comparable or lower crust within experimental error than the standard control composition.

Table 6 also summarizes data and the test procedure for hair feel. The data in Table 6 shows that a hair spray composition containing a carboxylated polyurethane resin having a low $M_w$ imparted better hand feel properties to sprayed hair than the control composition. It also was found that hand feel properties of sprayed hair was maximized for hair spray compositions containing a carboxylated polyurethane resin having a low $M_w$, and an R-value below about 0.75, i.e., about 0.55 to about 0.75.

does not adversely affect the carboxylated polyurethane resin, or the hair spray composition.

Table 7 illustrates the effects of adding a second hair fixative resin to the hair spray composition on composition viscosity and spray pattern. No adverse affects were observed.

TABLE 7

Hair Spray Compositions Containing a Low Molecular Weight Carboxylated Polyurethane and a Second Hair Fixative Resin

| Example No. | Polyurethane Resin A[27] (% wt) | Second Hair Fixative Resin[28] (% wt) | VOC (% wt) | Water (% wt) | Resin Ratio[29] | Viscosity (cs) | Spray Pattern |
|---|---|---|---|---|---|---|---|
| 1 | 2.00 | 1.00 | 55.0 | 42.0 | 0.50 | 6.74 | good |
| 2 | 2.00 | 1.00 | 80.0 | 17.0 | 0.50 | 4.58 | good |
| 3 | 4.00 | 2.00 | 55.0 | 39.0 | 0.50 | 11.88 | good |
| 4 | 4.00 | 2.00 | 80.0 | 14.0 | 0.50 | 7.22 | good |
| 5 | 1.00 | 2.00 | 55.0 | 42.0 | 2.00 | 8.45 | good |
| 6 | 1.00 | 2.00 | 80.0 | 17.0 | 2.00 | 5.34 | good |
| 7 | 2.00 | 4.00 | 55.0 | 39.0 | 2.00 | 12.59 | good |
| 8 | 2.00 | 4.00 | 80.0 | 14.0 | 2.00 | 8.19 | good |
| 9 | 2.25 | 2.25 | 55.0 | 40.5 | 1.00 | 9.81 | good |
| 10 | 2.25 | 2.25 | 80.0 | 15.5 | 1.00 | 5.79 | good |
| 11 | 1.50 | 1.50 | 67.5 | 29.5 | 1.00 | 5.56 | good |
| 12 | 3.00 | 3.00 | 67.5 | 26.5 | 1.00 | 9.61 | good |
| 13 | 3.00 | 1.50 | 67.5 | 28.0 | 0.50 | 6.64 | good |
| 14 | 1.50 | 3.00 | 67.5 | 28.0 | 2.00 | 7.83 | good |
| 15 | 2.25 | 2.25 | 67.5 | 28.0 | 1.00 | 7.68 | good |

[27]A carboxylated polyurethane resin having a weight average molecular weight of about 15,000 and an R-value of 0.65, prepared according to the method described in Example A;
[28]GANTREZ® A425, a partial butyl ester of a copolymer of vinyl methyl ether and maleic anhydride, available commercially from ISP, Wayne, NJ; and
[29]Ratio of second hair fixative resin to polyurethane resin.

Hair sprayed with the hair spray compositions also were tested for the amount of flakes or dust that form on the hair after combing hair that has been sprayed with the composition and dried. Table 6 shows that, in general, hair spray compositions containing a carboxylated polyurethane resin performed equally to the control composition. In particular, hair spray compositions containing a carboxylated polyurethane resin having an $M_w$ of about 10,000 to about 25,000 and an R-value of about 0.55 to about 0.75 outperformed the control composition.

The hair spray compositions containing an optional second hair fixative resin also impart good hold and hair set retention to treated hair and give the hair a natural feel. For example, a hair spray composition containing 3 wt. % of a carboxylated polyurethane resin having an $M_w$ of about 15,000 and an R-value of about 0.65, i.e., Polyurethane Resin A, when combined with 2 wt. % of GANTREZ® A425 provided equal or better set retention at 70% relative humidity and 25° C. than a control hair spray product containing the resin AMPHOMER. At 85% relative humidity, the identical hair spray composition provided equal or better hair set retention than a control hair spray product containing AMPHOMER. AMPHOMER is an acrylic copolymer resin and is widely used in commercial aerosol and pump hair spray products. Hair spray products containing AMPHOMER, therefore, are used as a control for comparing a hair spray compositions.

The presence of an optional second hair fixative resin imparts a stiffer feel to the hair. Several consumers prefer such a stiff feel as a "signal" that the hair has been treated. As shown below, the presence of a second hair fixative resin Examples 1–15 in Table 7 show that aerosol hair spray compositions containing a carboxylated polyurethane resin and a conventional, second hair fixative resin, and having a low VOC (i.e., 55% by weight) and a low viscosity, can be prepared. The second hair fixative resin is sufficiently solubilized, or dispersed, in the water-ethanol solvent, and the hair spray composition has a sufficiently low viscosity for effective application to the hair (e.g., see Example 7 containing 4.00% by weight of the second hair fixative resin in a 55% VOC composition and having a viscosity of 12.59 cs). Table 7 further shows a low composition viscosity and a good spray pattern for hair spray compositions containing a low molecular weight polyurethane resin (e.g., about 15,000), even when the resin ratio of second hair fixative resin to polyurethane resin is greater than one, over the entire VOC range of 55% to 80% by weight.

A hair spray composition containing an optional second hair fixative resin imparts a good feel to the hair and avoids excessive flaking and crust. Table 8 summarizes the results of tests using hair spray compositions containing 3% to 5% by weight of a low molecular weight polyurethane resin, 0 to 1% by weight GANTREZ A425 as the second hair fixative resin, and 55% ethanol. Hair sprayed with the resulting compositions, i.e., Examples 16–23, was tested for average crust, average feel, and average flaking.

The hair crust test measures the hardness and/or stiffness of hair sprayed with a hair spray composition. Hair spray compositions that provide natural, or reduced, crusts are desired. Hair crust was tested subjectively in this test wherein a group of trained judges evaluated hair tresses sprayed with a present hair spray composition containing a polyurethane resin and a second hair fixative resin, or with the control composition. The hair flaking test measures the amount of flakes or dust that form on the hair after combing hair that has been sprayed with the composition and dried.

TABLE 8

| Example | 16 | 17 | 18 | 19 | 20 | 21 | 22 | 23 |
|---|---|---|---|---|---|---|---|---|
| Ingredient | % wt/wt | | | | | | | |
| Ethanol | 55.00 | 55.00 | 55.00 | 55.00 | 55.00 | 55.00 | 55.00 | 55.00 |
| Polyurethane Resin A[27] | 3.00 | 3.00 | 3.00 | 5.00 | 4.00 | 4.00 | 5.00 | 5.00 |
| GANTREZ ® A425[28] | 0 | 0.50 | 1.00 | 0 | 0.50 | 1.00 | 0.50 | 1.00 |
| AMP | 0 | 0.09 | 0.18 | 0 | 0.09 | 0.18 | 0.09 | 0.18 |
| D.I. Water | 42 | 41.41 | 40.82 | 40 | 40.41 | 39.82 | 39.41 | 38.82 |
| Total | 100.00 | 100.00 | 100.00 | 100.00 | 100.00 | 100.00 | 100.00 | 100.00 |
| Performance | | | | | | | | |
| Avg. Crust[30] | 4.75 | 3.50 | 4.23 | n/a | 7.00 | 8.30 | 9.10 | 9.43 |
| Avg. Feel[31] | 4.00 | 2.60 | 3.33 | 9.00 | 5.50 | 5.66 | 7.50 | 8.66 |
| Avg. Flaking[32] | 7.00 | 3.33 | 4.5 | 9.00 | 6.80 | 6.33 | 7.66 | 8.83 |

[30]Average crust was evaluated by two to five judges compressing a treated hair curl between the fingers, and rated on a scale of 1 to 9, wherein 1 = natural hair and 10 = very crusty;
[31]Average feel was evaluated by two to five judges, for degree of raspiness, coating and gluing effect of treated hair tresses, and rated on a scale of 1 to 9, wherein 1 = natural hair and 10 = very raspy, coated and/or glued; and
[32]Average flaking was evaluated by two to five judges, wherein treated, dried hair tresses were combed and visually rated for amount of flaking.

The data summarized in Table 8 demonstrates that blending a carboxylated polyurethane with a second hair fixative resin (e.g., GANTREZ® A425) results in an improvement of the overall properties of the hair spray compositions.

Table 9 contains data for low VOC hair spray compositions containing a low molecular weight carboxylated polyurethane resin and a second hair fixative resin. Examples 24–31 in Table 9 demonstrate that blending a low molecular weight polyurethane with AMPHOMER results in improved overall properties of the hair spray compositions.

TABLE 9

| Example | 24 | 25 | 26 | 27 | 28 | 29 | 30 | 31 |
|---|---|---|---|---|---|---|---|---|
| Ingredient | % wt/wt | | | | | | | |
| Ethanol | 55.00 | 55.00 | 55.00 | 55.00 | 55.00 | 55.00 | 55.00 | 55.00 |
| Polyurethane Resin A[27] | 3.00 | 3.00 | 3.00 | 5.00 | 4.00 | 4.00 | 5.00 | 5.00 |
| AMPHOMER[33] | 0 | 0.50 | 1.00 | 0 | 0.50 | 1.00 | 0.50 | 1.00 |
| AMP | 0 | 0.09 | 0.18 | 0 | 0.09 | 0.18 | 0.09 | 0.18 |
| D.I. Water | 42.00 | 41.41 | 40.82 | 40.00 | 40.41 | 39.82 | 39.41 | 38.82 |
| Total | 100.00 | 100.00 | 100.00 | 100.00 | 100.00 | 100.00 | 100.00 | 100.00 |
| Performance | | | | | | | | |
| Avg. Crust[30] | 4.75 | 3.00 | 3.75 | n/a | 6.38 | 6.75 | 7.00 | 9.00 |
| Avg. Feel[31] | 4.0 | 4.25 | 4.88 | 9.0 | 7.10 | 7.50 | 8.50 | 8.75 |
| Avg. Flaking[32] | 7.0 | 2.92 | 3.25 | 9.0 | 6.00 | 6.50 | 7.86 | 8.75 |

[33]Octylacrylamide/acrylates/butylaminoethyl methacrylate copolymer, available from National Starch and Chemical Corp., Bridgewater, NJ.

Many modifications and variations of the invention as hereinbefore set forth can be made without departing from the spirit and scope thereof, and, therefore, only such limitations should be imposed as are indicated by the appended claims.

What is claimed is:

1. A hair spray composition consisting of:
   (a) about 0.25% to about 6% by weight of a carboxylated polyurethane resin;
   (b) about 0% to about 6% by weight of a second hair fixative resin;
   (c) about 0% to about 80% by weight of an alcohol; and
   (d) about 15% to about 99% by weight water;
   wherein the carboxylated polyurethane resin has a weight average molecular weight of about 10,000 to about 25,000, an acid value of about 7 to about 50 mg. KOH/g of resin, a melting point of about 40° C. to about 100° C., and is a reaction product of a mixture consisting essentially of:
   (i) about 10% to about 90% by weight of the mixture of a polyoxyalkylene diol having a number average molecular weight of about 400 to about 20,000;
   (ii) about 0.01% to about 20% by weight of the mixture of an alkylene glycol;
   (iii) about 3% to about 80% by weight of the mixture of an organic diisocyanate;
   (iv) about 1% to about 12% by weight of the mixture of a 2,2-di(hydroxymethyl)-alkanoic acid; and
   (v) about 0.1% to about 0.5% by weight of the mixture of water,
   wherein a ratio of isocyanate groups to hydroxyl groups is about 0.55 to about 0.75.

* * * * *